United States Patent [19]

Uno et al.

[11] Patent Number: 4,965,266
[45] Date of Patent: Oct. 23, 1990

[54] HETEROARYLCARBOXAMIDE DERIVATIVES, PROCESS FOR PREPARING THE SAME AND PHARMACEUTICAL COMPOSITION CONTAINING THE SAME

[75] Inventors: Hitoshi Uno, Takatsuki; Tatsuya Kon, Ashiya; Yoshinori Nishikawa, Ikeda; Tokuhiko Shindo, Nara; Hideo Nakamura, Tenri; Katsumi Ishii, Otsu, all of Japan

[73] Assignee: Dainippon Pharmaceutical Co., Ltd., Osaka, Japan

[21] Appl. No.: 296,083

[22] PCT Filed: Jan. 20, 1988

[86] PCT No.: PCT/JP88/00038
  § 371 Date: Oct. 18, 1988
  § 102(e) Date: Oct. 18, 1988

[87] PCT Pub. No.: WO88/05435
  PCT Pub. Date: Jul. 28, 1988

[30] Foreign Application Priority Data

Jan. 20, 1987 [JP] Japan .................................. 62-11128

[51] Int. Cl.$^5$ .................... A61K 31/495; C07D 401/14
[52] U.S. Cl. ..................................... 514/253; 514/252; 514/300; 514/312; 514/318; 544/360; 544/362; 544/363; 546/123; 546/156; 546/193
[58] Field of Search ...................... 544/360, 362, 363; 546/123, 156, 193; 514/252, 253, 300, 312, 318

[56] References Cited

U.S. PATENT DOCUMENTS

| | | | |
|---|---|---|---|
| 3,922,276 | 12/1975 | Duncan, Jr. et al. ................ | 546/226 |
| 3,943,141 | 3/1976 | Ellis et al. ........................... | 546/123 |
| 4,778,796 | 10/1988 | Uno et al. ............................ | 514/252 |

FOREIGN PATENT DOCUMENTS

| | | |
|---|---|---|
| 0113226 | 7/1984 | European Pat. Off. |
| 3242344 | 5/1984 | Fed. Rep. of Germany |
| 1433774 | 4/1976 | United Kingdom |

OTHER PUBLICATIONS

B. Riegel, et al., "The Synthesis of Some 4-Quinolinols and 4-Chloroquinolines by One Ethoxymethylenemalonic Ester Method",: *J. Am. Chem. Soc.*, 68: 1264–1266, 1946.

G. R. Lappin, "Cyclization of 2-Aminopyridine Derivatives. I. Substituted Ethyl 2-Pyridylaminomethylene-Malonates," *J. Am. Chem. Soc.*, 70: 3348–3350, 1948.

B. Marks & H. P. Schultz, "Quinoxaline Studies, II. The Preparation of 2-Hydroxy-3,6-Dimethylquinoxaline and 2-Hydroxy-3,7-Dimethylquinoxaline," *J. Am. Chem. Soc.*, 73: 1368–1370, 1951.

Levine, et al., "Effect of Combinations of Inbred Strain, Antigen, and Antigen Dose on Immune Responsiveness and Reagin Production in the Mouse," *Int. Arch. Allergy Appl. Immunology*, 39: 156–171, 1970.

E. E. Kilbourn & M. C. Seidel, "Synthesis of N-Alkyl-3-Carboxy-4-Pyridones," *J. Org. Chem.*, 37: 1145–1148, 1972.

S. Carboni, et al., "Synthesis and Biological Activity of Some 1,8-Naphthyridimes," *II. Farmaco E. Sci.*, 28: 722–732, 1973.

J. Perper, et al., "An Analysis of the Specificity in Pharmacological Inhibition of the Passive Cutaneous Anaphylaxis Reaction in Mice and Rats," *J. Pharm. Exp. ther.*, 193: 594–602, 1975.

K. J. Shah & E. A. Coats, "Design, Synthesis and Correlation Analysis of 7-Substituted 4-Hydroxyquinoline-3-Carboxylic Acids as Inhibitors of Cellular Respiration," *J. Med. Chem.*, 20: 1001–1006, 1977.

P. Hedqvist, et al., "Biological Profile of Leukotrienes $C_4$ and $D_4$" *Acta Physiol. Scand.*, 110: 331–333, 1980.

A. W. Ford-Hutchinson, et al., "Leukotriene B, a Potent Chemokinetic and Aggregating Substance Released from Polymorphonuclear Leukocytes," *Nature*, 286: 264–265, 1980.

A. Ueno, et al., "Species Difference in Increased Vascular Permeability by Synthetic Leukotriene $C_4$ and $D_4$," *Prostaglandins*, 21: 637–648, 1981.

(List continued on next page.)

*Primary Examiner*—Glennon H. Hollrah
*Assistant Examiner*—James H. Turnipseed
*Attorney, Agent, or Firm*—Scully, Scott, Murphy & Presser

[57] ABSTRACT

Heteroarylcarboxamide derivatives of the formula I:

$$\text{Het}-\text{CONH}-\text{A}-\text{N}\underset{\diagdown}{\diagup}\text{X} \quad (I)$$

wherein A means an alkylene group, X means $<NCHPh_2$ or $<C=CPh_2$ in which Ph means phenyl and (Het) means a group of the formulas:

[structures shown with $R_1$, $R_2$, $R_3$, $Y$]

in which Y means nitrogen atom or =CH—, $R_1$ means hydroxy, a lower alkoxy or mercapto, $R_2$ means hydrogen atom, a halogen atom, a lower alkyl group, a lower alkoxy group, nitro or cyano, $R_3$ means a lower alkyl group, provided that $R_2$ is attached at the 7-position when Y means nitrogen atom, or physiologically acceptable salts thereof, a process for preparing the same and a pharmaceutical composition containing the same as an active ingredient. The compounds of the present invention and salts thereof show an excellent antiallergic activity and thus are useful for the prophylaxis and treatment of allergic diseases.

16 Claims, No Drawings

OTHER PUBLICATIONS

T. Miyamoto & T. Obato, "New Inhibitors of 5-Kipoxygenase," Perspectives in Prostaglandin Research (Procedgs of Winter Seminar of the Japanese Inflammation Society,) ed. by Y. Shiokawa et al., Excerpta Medica, Amsterdam–Oxford–Princeton, pp. 78–80, 1983.

S. J. Coles et al., "Effects of Leukotrienes $C_4$ and $D_4$ on Glycoprotein and Lysozyme Secretion by Human Bronchial Mucosa," *Prostaglandins*, 25: 155–170, 1983.

Uno, et al., "Chemical Abstracts", vol. 110, 1988, col. 110: 23866r.

HETEROARYLCARBOXAMIDE DERIVATIVES, PROCESS FOR PREPARING THE SAME AND PHARMACEUTICAL COMPOSITION CONTAINING THE SAME

TECHNICAL FIELD

The present invention relates to novel and useful heteroarylcarboxamide derivatives which have an antiallergic activity based on 5-lipoxygenase inhibitory activity and the like.

BACKGROUND ART

British Patent No. 1,433,774 and U.S. Pat. No. 3,943,141 disclose 1,4-dihydro-4-oxo-N(1H-tetrazol-5-yl)-3quinolinecarboxamide derivatives and 1,4-dihydro-4-oxo-N-(1H-tetrazol-5-yl)-1,8-naphthyridine-3-carboxamide derivatives, respectively, as a useful antiallergic agent. DT-OS 3242344 discloses that alkylenediamine derivatives such as N-[3-[[2-(3,4-dimethoxyphenyl)ethyl]methylamino]propyl]-2-hydroxy-6-methylpyridine-3-carboxamide are useful for treatment of sinus tachycardia and ischemic heart diseases.

The mechanism of the development of allergic diseases such as bronchial asthma and allergic rhinitis have been generally thought as follows. In genetically specific individuals who are exposed to allergens such as pollen or mite, B-lymphocytes produce antigen-specific IgE in cooperation with macrophages and T-lymphocyte. The antigen-specific IgE binds to IgE receptors on the membrane of mast cells or basophiles. The bridging of IgE molecules by the re-invading antigen triggers the change of structure of cell membrane, the increment of membrane fluidity and the activation of various enzymes (including 5-lipoxygenase). Consequently, chemical mediators such as leukotrienes $C_4$, $D_4$, $E_4$ and $B_4$, histamine and prostaglandins are released from these cells, and cause the syndromes in allergic disease.

Among these chemical mediators, leukotrienes $C_4$, $D_4$ and $E_4$ cause strongly the contraction of bronchial smooth muscle [P. Hedqvist et al., Acta Physiol. Scand., 110, 331 (1980)], increased vascular permeability [A. Ueno et al., Prostaglandins, 21, 637 (1981)], and secretion of mucus [S. J. Coles et al., Prostaglandins, 25, 155 (1983)], and leukotriene $B_4$ does leukocyte emigration [A. W. Ford-Hutchinson et al., Nature, 286, 264 (1980)], playing an important role in the development of allergic diseases. Compounds that inhibit the biosynthesis and release of leukotrienes or inhibit the binding of leukotrienes to their receptors may be useful for the prophylaxis or treatment of allergic diseases. 5-Lipoxygenase is an enzyme which catalyzes an early step of biosynthesis of leukotrienes, that is, the conversion of arachidonic acid into 5-hydroperoxyeicosatetraenoic acid.

The present inventors have intensively studied to find out a compound which can inhibit the 5-lipoxygenase and, as a result, have found that the aromatic heterocyclic carboxylic acid derivatives represented by the following formula (I) are fit for the above purpose and thus completed the present invention.

DISCLOSURE OF THE INVENTION

The present invention provides heteroarylcarboxamide derivatives of the formula (I):

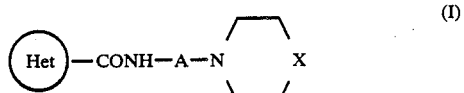

wherein A means an alkylene group having 3 to 5 carbon atoms, X means $<NCHPh_2$ or $<C=CPh_2$ in which Ph means phenyl and (Het) means the formulas:

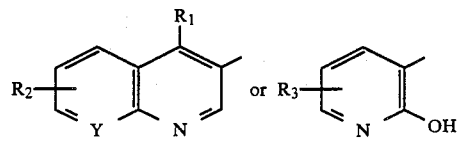

in which Y means nitrogen atom or =CH—, $R_1$ means hydroxy, an alkoxy group having 1 to 6 carbon atoms or mercapto, $R_2$ means hydrogen atom, a halogen atom, an alkyl group having 1 to 6 carbon atoms, an alkoxy group having 1 to 6 carbon atoms, nitro or cyano, $R_3$ means an alkyl group having 1 to 6 carbon atoms, provided that $R_2$ is attached at the 7-position when Y means nitrogen atom, and physiologically acceptable salts thereof, a process for preparation thereof and a pharmaceutical composition containing the same as an active ingredient.

The physiologically acceptable salts of the compounds represented by the formula (I) include, for example, inorganic acid salts such as hydrochloride, hydrobromide, hydroiodide, sulfate, phosphate and the like, and organic acid salts such as oxalate, maleate, fumarate, lactate, malate, citrate, tartrate, benzoate, methanesulfonate and the like. Since the compounds of the present invention may exist in the form of hydrate or solvate, these hydrate and solvate are also included in the present invention.

Since the compounds of the present invention, excepting those of the formula (I) wherein $R_1$ is an alkoxy group having 1 to 6 carbon atoms, may exist in the form of the tautomer represented by the following formula (I'), these tautomers are also included in the compound of the present invention.

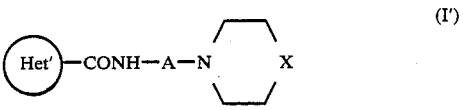

wherein A and X mean the same as defined above, (Het') means a group of the formula:

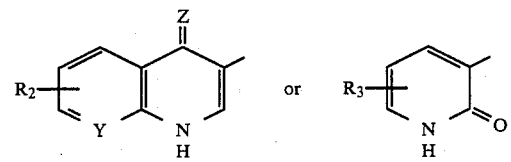

in which Y, $R_2$ and $R_3$ are the same as defined above, and Z means oxygen atom or sulfur atom.

In the following description, the structure and name of the compounds of the present invention are indicated by the formula (I).

The terms in the specification are explained in the following.

An alkylene group, an alkyl group and an alkoxy group may be either a straight chain or a branched chain. The "alkylene group" includes, for example, trimethylene, tetramethylene, pentamethylene and the like, preferably tetramethylene. The "alkoxy group" includes, for example, methoxy, ethoxy, propoxy, isopropoxy, butoxy, pentyloxy and the like, preferably those having 1 to 4 carbon atoms. The "halogen atom" means fluorine, chlorine, bromine and iodine, preferably fluorine, chlorine and bromine. The "alkyl group" includes, for example, methyl, ethyl, propyl, isopropyl, butyl, pentyl and the like, preferably those having 1 to 4 carbon atoms.

Preferable compounds of the present invention include those of the formula (I) wherein A is tetramethylene and physiologically acceptable salts thereof.

More preferable compounds of the present invention include the compounds of the formula (Ia):

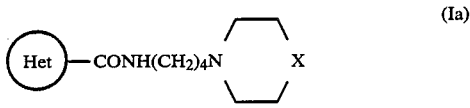

wherein X means the same as defined above, $(Het)$ means a group of the formula:

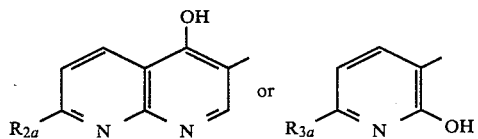

in which $R_{2a}$ and $R_{3a}$ mean an alkyl group having 1 to 4 carbon atoms, respectively, and physiologically acceptable salts thereof.

Another more preferable compounds of the present invention include the compounds of the formula (Ib):

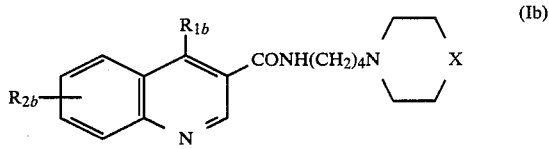

wherein X means the same as defined above, $R_{1b}$ means hydroxy, an alkoxy group having 1 to 4 carbon atoms or mercapto, $R_{2b}$ means hydrogen atom, hydroxy, an alkyl group having 1 to 4 carbon atoms, an alkoxy group having 1 to 4 carbon atoms or cyano, and physiologically acceptable salts thereof.

Particularly preferable compounds of the present invention include the following compounds and physiologically acceptable salts thereof.

N-[4-(4-Diphenylmethylene-1-piperidyl)butyl]-4-hydroxy-7-methyl-1,8-naphthyridine-3-carboxamide,
N-[4-(4-Diphenylmethyl-1-piperazinyl)butyl]-4-hydroxy-7-methyl-1,8-naphthyridine-3-carboxamide,
N-[4-(4-Diphenylmethyl-1-piperazinyl)butyl]-4-hydroxy-8-methoxyquinoline-3-carboxamide, and
N-[4-(4-Diphenylmethyl-1-piperazinyl)butyl]-2-hydroxy-6-isopropylpyridine-3-carboxamide The compounds of the present invention can be prepared, for example, by the following process.

The compound of the formula (II):

wherein $(Het)$ means the same as defined above, or a reactive derivative thereof is reacted with an amine of the formula (III):

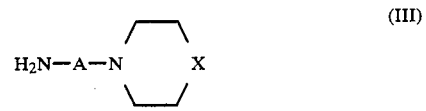

wherein A and X mean the same as defined above to prepare the compounds of the formula (I).

The reactive derivatives of the compounds of the formula (II) include, for example, activated esters, acid anhydrides, acid halides (especially acid chloride) and lower alkyl esters. Suitable examples of the activated esters include p-nitrophenyl ester, 2,4,5-trichlorophenyl ester, pentachlorophenyl ester, cyanomethyl ester, N-hydroxysuccinimide ester, N-hydroxyphthalimide ester, 1-hydroxybenzotriazole ester, N-hydroxy-5-norbornene-2,3-dicarboximide ester, N-hydroxypiperidine ester, 8-hydroxyquinoline ester, 2-hydroxyphenyl ester, 2-hydroxy-4,5-dichlorophenyl ester, 2-hydroxypyridine ester, 2-pyridylthiol ester and the like. The acid anhydrides include both symmetric acid anhydrides and mixed acid anhydrides. Suitable examples of the mixed acid anhydrides include those with alkyl chloroformates such as ethyl chloroformate or isobutyl chloroformate, with aralkyl chloroformates such as benzyl chloroformate, with aryl chloroformates such as phenyl chloroformate, with alkanoic acids such as isovaleric acid or pivalic acid, and the like.

In case that the compound of the formula (II) is employed as it is, the compound (II) can be reacted with the compound (III) in the presence of a condensing agent such as dicyclohexylcarbodiimide, 1-ethyl-3-(3-dimethylaminopropyl)carbodiimide hydrochloride, N,N'-carbonyldiimidazole, 1-ethoxycarbonyl-2-ethoxy-1,2-dihydroxyquinoline or the like. When dicyclohexylcarbodiimide or 1-ethyl-3-(3-dimethylaminopropyl)carbodiimide hydrochloride is employed as the condensing agent, the reaction may be conducted with addition of N-hydroxysuccinimide, 1-hydroxybenzotriazole, 3-hydroxy-4-oxo-3,4-dihydro-1,2,3-benzotriazine, N-hydroxy-5-norbornene-2,3-dicarboximide or the like.

The reaction between the compound of the formula (II) or the reactive derivative thereof and the amine of the formula (III) is carried out without a solvent or in a suitable solvent. Although an employed solvent would vary depending on the kinds of the starting compounds and the like, the solvent used in the reaction of the present invention includes, for example, aromatic hydrocarbons such as benzene, toluene and xylene; ethers such as diethyl ether, diisopropyl ether, tetrahydrofuran and dioxane; halogenated hydrocarbons such as methylene chloride and chloroform; ethyl acetate, acetonitrile, dimethylformamide, dimethyl sulfoxide, water and the like. These solvents are employed alone or in combination of two or more thereof. The reaction may optionally be carried out in the presence of a base. The base includes alkali metal bicarbonates such as sodium bicarbonate or potassium bicarbonate, alkali metal carbonates such as sodium carbonate or potassium carbonate, or organic bases such as triethylamine, tributylamine, diisopropylethylamine, or N-methylmorpholine. An excess amount of the amines of the formula (III) may also be employed as the base. The reaction temperature usually ranges from about −40° C. to about 200° C., preferably from about −20° C. to about 150° C., though it may vary depending on the kinds of the starting compounds and the like.

The starting compounds (II) can be prepared, for example, by the processes as described in J. Am. Chem. Soc., 70, 3348 (1948) and ibid., 68, 1264 (1946). The starting compounds (III) can be prepared, for example, by the process as described in Reference Example.

The compounds prepared in the above process can be isolated and purified by the conventional methods such as chromatography, recrystallization or reprecipitation.

The compounds of the formula (I) are obtained in the form of a free base or salt, a hydrate or a solvate depending on the conditions of the reaction and the treatment, and the like. The salt can be converted into a free base by the conventional procedure, for example, by treating with a base such as alkali metal carbonates. On the other hand, the free base can be converted into a salt by treating with various acids in accordance with the conventional procedure.

In the following, the pharmacological activities of the compounds of the present invention are illustrated by pharmacological tests on the typical compounds of the present invention and ketotifen fumarate which is a commercially available antiallergic agent.

EXPERIMENT 1

Inhibitory effect on 5-lipoxygenase activity (antiallergic activity in vitro)

This experiment was carried out by the method of Miyamoto and Obata ["Perspectives in Prostaglandin Research", ed. by Y. Shiokawa et al., Excerpta Medica, Amsterdam-Oxford-Princeton, 1983, p.78] with minor modifications.

A cytosol fraction of peritoneal exudate cell from male Hartley guinea pig (weighing 400 to 700 g) was used as 5-lipoxygenase. As a standard reaction solution, a mixture of 50 mM potassium phosphate buffer (pH 7.4), 1 mM calcium chloride, 1 mM glutathione, 1 mM adenosine triphosphate, 10 $\mu$M indomethacin and the enzyme was used. To the reaction solution was added 0.02 $\mu$Ci of [1−$^{14}$C] arachidonic acid and the mixture was incubated at 30° C. for 5 minutes, followed by adding 0.6 ml of a cold solution comprising diethyl ether methanol −0.2 M citric acid (30 : 4 : 1) to terminate the reaction. The organic layer (300 $\mu$l) was subjected to a thin layer chromatography plate on silica gel 60 F$_{254}$ (E. Merck, West Germany) and, after developing, a radioactivity was measured by means of radiochromatogram scanner (Packard, U.S.A.) 5-Lipoxygenase activity was calculated by the following equation.

$$\text{5-Lipoxygenase activity} = \frac{\text{Radioactivity under a peak of 5-HETE}}{\text{Radioactivity under all peaks}}$$

5-HETE: 5-hydroxyeicosatetraenoic acid

The inhibitory rate was calculated from 5-lipoxygenase activities without vs. with the test compound ($10^{-5}$ M). The results are shown in Table 1 in terms of mean value of 3 to 6 experiments.

TABLE 1

| | 5-Lipoxygenase Inhibitory Activity | | |
|---|---|---|---|
| Test Comp. | 5-Lipoxygenase inhibition (%) | Test Comp. | 5-Lipoxygenase inhibition (%) |
| 1* | 96.8 | 12 | 83.7 |
| 2 | 79.6 | 14 | 93.7 |
| 3 | 91.3 | 15 | 93.0 |
| 4 | 95.4 | 16 | 90.6 |
| 5 | 80.3 | 17 | 95.3 |
| 6 | 75.1 | 18 | 93.2 |
| 7** | 92.1 | 19 | 92.8 |
| | 84.7 | 20 | 94.8 |
| 8 | 93.3 | 21 | 67.9 |
| 9 | 88.3 | Ketotifen fumarate*** | 11.5 |

*This means the compound of Example 1 (hereinafter the same)
**The upper value is concerned with 5-cyano compound and the lower value concerned with 7-cyano compound.
***The concentration is $10^{-4}$ M.

As is clear from Table 1, the compounds of the present invention inhibited strongly 5-lipoxygenase activity. On the other hand, ketotifen fumarate did not show any significant inhibitory activity even at the concentration of $10^{-4}$ M.

EXPERIMENT 2

Inhibitory effect on passive cutaneous anaphylaxis (PCA) (antiallergic activity in vivo)

This experiment was carried out by the method of Perper et al., [J. Pharmacol. Exp. Ther., 193, 594 (1975)].

Male Wistar rats (weighing 130 to 190 g) were injected with a dilute solution (0.1 ml) of mouse antiserum to egg albumin, which was prepared by the method of Levine et al. [Int. Arch. Allergy Appl. Immunol., 39, 156 (1970)], in two sites of the shaved ventral skin. Forty-eight hours later, 0.5% Evan's blue solution (1 ml) containing 2 mg of egg albumin was intravenously injected to tail vein of the animal. Thirty minutes after the dye injection, abdominal skin was peeled off and the area of the blueing lesions was measured. In each rat, a mean value of the two lesions was regarded as the response of the rat. The test compounds in a dose of 20 mg/kg, dissolved or suspended in a 0.5% aqueous tragacanth solution, were orally administered 1 hour prior to the dye injection.

Table 2 shows an inhibitory rate obtained by comparing the response of the rats given each test compound with that of the rats given only a 0.5% aqueous tragacanth solution (control group).

TABLE 2

| | PCA Inhibitory Activity | | |
|---|---|---|---|
| Test comp. | PCA inhibition (%) | Test comp. | PCA inhibition (%) |
| 1* | 88.3 | 6 | 93.0 |
| 2 | 80.7 | 10 | 84.8 |
| 3 | 56.0 | Ketotifen fumarate | 54.7 |

*This means the compound of Example 1 (hereinafter the same).

As is clear from Table 2, the compounds of the present invention showed a PCA inhibitory activity equivalent to or more potent than that of ketotifen fumarate.

EXPERIMENT 3

Acute toxicity

Five male ddY mice weighing 25 to 29 g were used in each group. A fixed amount of the compound of Example 1, 3 or 6 suspended in a 0.5% aqueous tragacanth solution was orally administered and a death of the animals was observed for 7 days after the administration.

As a result, no death was observed for the administration of 1000 mg/kg of each compound of Example 1, 3 or 6. Therefore, the dose for showing an acute toxicity of these compounds is much higher than that for showing the antiallergic activity.

Since the compounds of the formula (I) and physiologically acceptable salts thereof show an excellent antiallergic activity mainly based on the 5-lipoxygenase inhibitory activity with less toxicity, they can be used as an antiallergic agent for the prophylaxis and treatment of allergic diseases such as bronchial asthma, allergic rhinitis, urticaria, atopic dermatitis, eczema and allergic ophthalmia.

The compounds of the formula (I) and physiologically acceptable salts thereof may be administered by any route of oral administration, parenteral administration, intrarectal administration and topical administration, preferably by oral or topical administration. A dose of the compounds of the formula (I) or salts thereof usually ranges from 0.005 to 40 mg/kg/day, preferably from 0.01 to 5 mg/kg/day, though it may vary depending on the kinds of the compounds, administration routes, severity of diseases or age of patients and the like. The compounds of the formula (I) or salts thereof are usually administered in the form of a pharmaceutical composition in admixture with pharmaceutically acceptable carriers. The pharmaceutically acceptable carriers include substances which are conventionally employed in the field of the pharmaceutical preparations and do not react with the compound of the formula (I) or the salts thereof. Suitable examples of the carriers are lactose, glucose, mannitol, dextrin, cyclodextrin, starches, sucrose, magnesium aluminosilicate tetrahydrate, synthetic aluminum silicate, microcrystalline cellulose, sodium carboxymethylcellulose, hydroxypropyl starch, calcium carboxymethylcellulose, ion exchange resin, methylcellulose, gelatin, acacia, hydroxypropyl cellulose, substituted hydroxypropyl cellulose, hydroxypropyl methylcellulose, polyvinylpyrrolidone, polyvinyl alcohol, light anhydrous silicic acid, magnesium stearate, talc, tragacanth, bentonite, veegum, carboxyvinyl polymer, titanium dioxide, sorbitan fatty acid esters, sodium lauryl sulfate, glycerin, glycerin fatty acid esters, anhydrous lanolin, glycero-gelatin, polysolbate, macrogol, vegetable oils, waxes, liquid paraffin, white petrolatum, fluorocarbons, nonionic surfactants, propylene glycol, water and the like. The pharmaceutical composition may be in the dosage form of tablets, capsules, granules, powders, syrups, suspensions, suppositories, ointments, creams, gels, adhesive preparations, inhalants, injections and the like. These compositions can be prepared by a conventional method. The liquid preparations may be in the form which is dissolved or suspended in an appropriate solvent such as water or others when used. The tablets and granules may be coated with a conventional coating material in a usual manner. The injections are usually prepared by dissolving the physiologically acceptable salts of the compounds of the formula (I) in water, but occasionally in physiological saline or a glucose solution, to which buffering agents or preservatives may optionally be added.

These compositions may contain the compounds of the formula (I) or the physiologically acceptable salts thereof at a ratio of not less than 0.2 %, preferably in the range of from 0.5 to 70 %. These compositions may also contain other ingredients useful for the treatment.

Best Mode for Carrying out the Invention

The present invention is illustrated by the following Examples and Reference Example, but should not be construed to be limited to these Examples. The identification of the compounds was carried out by elementary analysis, mass spectrum, IR spectrum, NMR spectrum and the like.

EXAMPLE 1

Preparation of N-[4-(4-diphenylmethylene-1-piperidyl)butyl]-4-hydroxy-7-methyl-1,8-naphthyridine-3-carboxamide•1/4 hydrate To 4-hydroxy-7-methyl-1,8-naphthyridine-3-carboxylic acid (0.77 g) is added dry chloroform (30 ml) and thereto is added triethylamine (0.76 g) with stirring at room temperature. The solution is kept at below −5° C. and thereto is added dropwise ethyl chloroformate (0.81 g), and the mixture is stirred for 2 hours. After 4-(4-diphenylmethylene-1-piperidyl)butylamine (1.2 g) is added gradually, the mixture is stirred at below −5° C. for 1 hour and further at room temperature overnight. After insoluble substances are filtered off, the filtrate is concentrated and the residue is subjected to silica gel column chromatography, followed by elution with chloroform - methanol (40 : 1) to give oils. The crystallized product is taken and recrystallized from toluene to give the desired compound (0.6 g). m.p. 168° to 170° C.

EXAMPLE 2

Preparation of N-[4-(4-diphenylmethyl-1-piperazinyl)butyl]-4-hydroxy-7-methyl-1,8-naphthyridine-3-carboxamide•1/2 hydrate To 4-hydroxy-7-methyl-1,8-naphthyridine-3-carboxylic acid (0.63 g) is added dry chloroform (30 ml) and thereto is added triethylamine (0.63 g) with stirring at room temperature. The solution is kept at below −5° C. and thereto is added dropwise ethyl chloroformate (0.67 g), and the mixture is stirred for 2 hours. After 4-(4-diphenyl- methyl-1-piperazinyl)butylamine (1 g) is added gradually, the mixture is stirred at below −5° C. for 1 hour and further at room temperature overnight. After insoluble substances are filtered off, the filtrate is concentrated and the residue is subjected to silica gel column chromatography, followed by elution with chloroform - methanol (40 : 1) to give oils. The crystallized product is taken and recrystallized from acetonitrile to give the desired compound (0.3 g). m.p. 202° to 205° C.

EXAMPLE 3

Preparation of N-[4-(4-diphenylmethyl-1-piperazinyl)butyl]-4-hydroxy-8-methoxyquinoline-3-carboxamide To 4-hydroxy-8-methoxyquinoline-3-carboxylic acid (1.0 g) is added dry pyridine (40 ml) and the mixture is heated at 80° C. Thereto is added p-nitrophenyl trifluoroacetate (2.6 g) and the mixture is stirred at the same temperature for 1 hour. After the mixture is allowed to cool, the precipitated crystals are filtered and washed with diethyl ether to give an activated ester. Thereto is added dry dimethylformamide (30 ml), followed by adding 4-(4- diphenylmethyl-1-piperazinyl)butylamine (3.5 g) with stirring at room temperature. After the reaction mixture is stirred for 1 hour, the dimethylformamide is distilled off. Chloroform is added to the residue and the chloroform solution is washed with water, dried over anhydrous magnesium sulfate and then concentrated. The residue is subjected to silica gel column chromatography, followed by elution with chloroform - triethylamine (50 : 1). The obtained crystals are recrystallized from ethanol to give the desired compound (1.02 g). m.p. 209° to 212° C.

EXAMPLE 4

Preparation of N-[4-(4-diphenylmethyl-1-piperazinyl)butyl]-4,5-dihydroxyquinoline-3-carboxamide N,N'-Carbonyldiimidazole (1.2 g) is added to a solution of 4,5-dihydroxyquinoline-3-carboxylic acid (0.7 g), which is prepared according to the method described in Japanese Patent First Publication No. 65874/1981, in dry dimethyl sulfoxide (30 ml) and the mixture is stirred at room temperature for 30 minutes. 4-(4-Diphenylmethyl-1-piperazinyl)butylamine (2.2 g) is added to the reaction mixture and the mixture is stirred at room temperature for 6 hours, and thereto is added water (about 200 ml), and the mixture is extracted with chloroform. The organic layer is dried over anhydrous magnesium sulfate and the solvent is distilled off. The residue is subjected to silica gel column chromatography, followed by elution with chloroform - methanol (30 : 1). The obtained crystals are recrystallized from isopropyl alcohol to give the desired compound (0.72 g). m.p. 215° to 218° C.

EXAMPLE 5

Preparation of N-[4-(4-diphenylmethyl-1-piperazinyl)butyl]-4-methoxyquinoline-3-carboxamide•1/4 hydrate To 4-hydroxyquinoline-3-carboxylic acid (2.0 g) is added phosphorus oxychloride (16 ml) and the mixture is refluxed with stirring for 30 minutes. After cooling, the reaction mixture is poured into ice-water and the precipitated crystals are filtered and dried. These crystals are suspended in absolute methanol (40 ml) and the resulting mixture is refluxed with stirring for 2.5 hours and allowed to cool. The precipitated crystals are collected to give 4-methoxyquinoline-3-carboxylic acid (1.8 g).

To a suspension of 4-methoxyquinoline-3-carboxylic acid (0.5 g) in methylene chloride (10 ml) is added thionyl chloride (0.29 g) and the mixture is refluxed with stirring for 30 minutes and then concentrated. To the residue is added toluene (25 ml), and to the mixture is added with stirring a solution of 4-(4-diphenylmethyl-1-piperazinyl)butylamine (0.8 g) in toluene (3 ml) at room temperature. After stirring for 1 hour, the reaction mixture is concentrated, neutralized with 10% aqueous potassium carbonate and then extracted with chloroform. The organic layer is washed with water, dried over anhydrous magnesium sulfate and then concentrated. The residue is subjected to silica gel column chromatography, followed by elution with chloroform - methanol (30 : 1). Recrystallization from toluene gives the desired compound (0.46 g). m.p. 210° to 212° C.

EXAMPLE 6

Preparation of N-[4-(4-diphenylmethyl-1-piperazinyl)butyl]-2-hydroxy-6-isopropylpyridine-3carboxamide Dry pyridine (30 ml) is added to 2-hydroxy-6-isopropylpyridine-3-carboxylic acid (1.0 g), prepared according to the method described in J. Am. Chem. Soc., 73, 1368 (1951), and the mixture is heated at 80° C. Thereto is added p-nitrophenyl trifluoroacetate (2.9 g) and the mixture is stirred at 80° C. for 1 hour. The mixture is allowed to cool and the precipitated crystals are filtered and washed with diethyl ether to give an activated ester. Dry dimethylformamide (30 ml) is added thereto and 4-(4-diphenylmethyl-1-piperazinyl)butylamine (1.8 g) is further added with stirring at room temperature. After stirring the reaction mixture for 1 hour, dimethylformamide is distilled off. Chloroform is added to the residue and the chloroform solution is washed with water, dried over anhydrous magnesium sulfate and then concentrated. The residue is subjected to silica gel column chromatography, followed by elution with chloroform - methanol (30 : 1). The obtained crystals are recrystallized from acetonitrile to give the desired compound (1.6 g). m.p. 184.5° to 185.5° C.

EXAMPLE 7

Preparation of N-[4-(4-diphenylmethyl-1-piperazinyl)butyl]-5-cyano-4-hydroxyquinoline-3-carboxamide and N-[4-(4-diphenylmethyl-1-piperazinyl)butyl]-7-cyano-4-hydroxyquinoline-3-carboxamide In accordance with the method described in J. Med. Chem., 20, 1001 (1977), a 1:1 mixture of 5-cyano-4-hydroxy- quinoline-3-carboxylic acid and 7-cyano-4-hydroxyquinoline3-carboxylic acid (confirmed by NMR spectrum) is prepared from m-cyanoaniline.

In the same manner as described in Example 1, the above mixture and 4-(4-diphenylmethyl-1-piperazinyl)butylamine are reacted in place of 4-hydroxy-7-methyl-1,8-naphthyridine-3-carboxylic acid and 4-(4-diphenyl-methylene-1-piperidyl)butylamine in Example 1 respectively. Insoluble substances are filtered off and then the filtrate is concentrated. The residue is subjected to silica gel column chromatogaphy, followed by elution with chloroform methanol (30 : 1). From the first eluted fraction there is obtained N-[4-(4-diphenylmethyl-1-piperazinyl)butyl]-7-cyano-4-hydroxyquinoline-3-carboxamide, which is recrystallized from acetonitrile to give a product of m.p. 223 to 225° C. From the subsequent fraction there is obtained N-[4-(4-diphenylmethyl-1-piperazinyl)butyl]-5-cyano-4-hydroxyquinoline-3-carboxamide, which is recrystallized from acetonitrile to give a product of m.p. 232 to 234° C. (dec.).

EXAMPLE 8

Preparation of N-[4-(4-diphenylmethylene-1piperidyl)butyl]-4-hydroxy-8-methoxyquinoline-3-carboxamide•fumarate The procedures of Example 1 are repeated except that 4-hydroxy-8-methoxyquinoline-3-carboxylic acid is employed in place of 4-hydroxy-7-methyl-1,8-naphthyridine-3-carboxylic acid to give N-[4-(4-diphenylmethylene-1-piperidyl)butyl]-4-hydroxy-8-methoxyquinoline-3-carboxamide, which is converted into fumarate in a usual manner. The fumarate is recrystallized from ethanol - diethyl ether to give the desired compound. m.p. 232° to 236° C.

EXAMPLE 9

Preparation of
N-[4-(4-diphenylmethyl-1-piperazinyl)butyl]-4-mercapto-7-methyl-1,8-naphthyridine-3-carboxamide•fumarate•1/2 hydratet The procedures of Example 1 are repeated except that 4-mercapto-7-methyl-1,8-naphthyridine-3-carboxylic acid, prepared according to the method described in Farmaco. Ed. Sci., 28, 722 (1973), and 4-(4-diphenylmethyl-1-piperazinyl)butylamine are employed in place of 4-hydroxy-7-methyl-1,8-naphthyridine-3-carboxylic acid and 4-(4-diphenylmethylene-1-piperidyl)butylamine to give N-[4-(4-diphenylmethyl-1-piperazinyl)butyl]-4-mercapto-7-methyl-1,8-naphthyridine-3-carboxamide as oils, which is converted into fumarate in a conventional manner. The fumarate is recrystallized from ethanol - water to give the desired compound. m.p. 209° to 212° C.

EXAMPLE 10

Preparation of
N-[4-(4-diphenylmethyl-1-piperazinyl)butyl]-2-hydroxy-6-methylpyridine-3-carboxamide The procedures of Example 6 are repeated except that 2-hydroxy-6-methylpyridine-3-carboxylic acid, prepared in accordance with the method described in J. Org. Chem., 37, 1145 (1972), is employed in place of 2-hydroxy-6-isopropylpyridine-3-carboxylic acid to give the desired compound. m.p. 213° to 214° C. (recrystallized from toluene)

EXAMPLE 11

Preparation of
N-[4-(4-diphenylmethyl-1-piperazinyl)butyl]-4-hydroxy-7-methoxy-1,8-naphthyridine-3-carboxamide•1/4 hydrate The procedures of Example 2 are repeated except that 4-hydroxy-7-methoxy-1,8-naphthyridine-3-carboxylic acid is employed in place of 4-hydroxy-7-methyl-1,8-naphthyridine-3-carboxylic acid to give the desired compound. m.p. 205° to 208° C. (recrystallized from acetonitrile)

EXAMPLES 12 TO 23

Employing the corresponding starting materials, the procedures of Examples 1 to 6 are repeated to give the compounds shown in Table 3.

In Table 3, the following abbreviations are used to simplify the description.
AN : Acetonitrile
CH : Chloroform
E : Diethyl ether
IA : Isopropyl alcohol
M : Methanol
T : Toluene

TABLE 3

| Example | $R_2$ | Q | m.p. (°C.) (recrystal. solv.) |
|---|---|---|---|
| 12 | H | — | 204–208 (AN) |
| 13 | 6-Cl | — | 173–175 (AN) |
| 14 | 6-CH$_3$ | ¾H$_2$O | 108–110 (T-E) |
| 15 | 7-CH$_3$ | — | 217–219 (T) |
| 16 | 8-CH$_3$ | — | 223–225 (T) |
| 17 | 6-i-C$_3$H$_7$ | — | 119–122 (T) |
| 18 | 6-OCH$_3$ | — | 148–151 (T) |
| 19 | 7-OCH$_3$ | 1/6 i-C$_3$H$_7$OH.¼H$_2$O | 168–170 (IA) |
| 20 | 8-OC$_4$H$_9$ | — | 199–201 (T) |
| 21 | 6-CN | — | 205–207 (T) |
| 22 | 8-CN | — | 230–232 (T) |
| 23 | 8-NO$_2$ | ¼H$_2$O | 219–223 (CH-M) |

The starting materials in Examples 1 and 8 are prepared by the method described in the following Reference Example.

REFERENCE EXAMPLE

Preparation of
4-(4-diphenylmethylene-1-piperidyl)butylamine

4-Diphenylmethylenepiperidine (9.5 g), N-(4-bromobutyl)phthalimide (16 g), sodium iodide (8 g) and potassium carbonate (9 g) are added to methyl ethyl ketone (200 ml) and the mixture is refluxed with stirring for 4 hours. The reaction mixture is concentrated and water (150 ml) is added to the residue. The aqueous layer is extracted three times with chloroform (each 100 ml). The combined extracts are dried over anhydrous magnesium sulfate and then concentrated. The residue is subjected to silica gel column chromatography, followed by elution with chloroform to give N-[4-(4-diphenylmethylene-1-piperidyl)butyl]phthalimide (13.7 g).

The obtained phthalimide compound (13.7 g) and hydrazine monohydrate (2.5 g) are added to ethanol (34 ml) and the mixture is refluxed with stirring for 2 hours. After cooling, a small amount of water is added to the reaction mixture and the solvent is distilled off under reduced pressure. Chloroform (200 ml) is added to the residue and the insoluble substances are filtered off and washed twice with chloroform (each 50 ml). The filtrate and the washings are combined together, washed with water, dried over anhydrous magnesium sulfate and concentrated to give the desired compound (12 g). Mass spectrum m/z: 320 (M+)

EXAMPLE 24

| | per 1000 tablets |
|---|---|
| N-[4-(4-Diphenylmethylene-1-piperidyl)-butyl]-4-hydroxy-7-methyl-1,8-naphthyridine-3-carboxamide.¼ hydrate | 1 g |
| Corn starch | 29 g |
| Lactose | 55 g |
| Microcrystalline cellulose | 11 g |
| Hydroxypropyl cellulose | 3 g |
| Light anhydrous silicic acid | 0.5 g |

-continued

| | per 1000 tablets |
|---|---|
| Magnesium stearate | 0.5 g |

In accordance with a conventional method, the above components are blended, granulated and compressed to prepare 1000 tablets of each 100 mg.

EXAMPLE 25

| | per 1000 capsules |
|---|---|
| N-[4-(4-Diphenylmethyl-1-piperazinyl)-butyl]-4-hydroxy-7-methyl-1,8-naphthyridine-3-carboxamide.½ hydrate | 1 g |
| Corn starch | 107 g |
| Lactose | 65 g |
| Hydroxypropyl cellulose | 5 g |
| Light anhydrous silicic acid | 1 g |
| Magnesium stearate | 1 g |

In accordance with a conventional method, the above components are blended, granulated and filled in 1000 capsules to prepare capsules of each 180 mg.

EXAMPLE 26

| | ointments |
|---|---|
| N-[4-(4-Diphenylmethyl-1-piperazinyl)-butyl]-2-hydroxy-6-isopropylpyridine-3-carboxamide | 5 g |
| Liquid paraffin | 10 g |
| White petrolatum | 85 g |

In accordance with a conventional method, the above components are blended to prepare 5% ointments.

Industrial Applicability

As mentioned above, the compounds of the formula (I) of the present invention and physiologically acceptable salts thereof are useful for the prophylaxis and treatment of allergic diseases of mammals including human as an antiallergic agent.

We claim:

1. A compound of the formula (I):

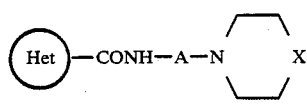

wherein A means an alkylene group having 3 to 5 carbon atoms, X means >NCHPh₂ or >C=CPh₂ in which Ph means phenyl and (Het) means a group of the formulas:

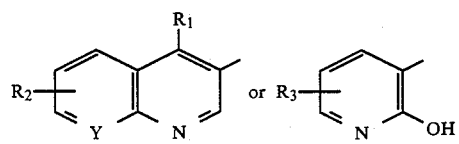

in which Y means nitrogen atom or =CH—, $R_1$ means hydroxy or mercapto, $R_2$ means hydrogen atom, a halogen atom, hydroxy, an alkyl group having 1 to 6 carbon atoms, an alkoxy group having 1 to 6 carbon atoms, nitro or cyano, $R_3$ means an alkyl group having 1 to 6 carbon atoms, provided that $R_2$ is attached at the 7-position when Y means nitrogen atom, or a physiologically acceptable salt thereof.

2. The compound according to claim 1 wherein A is tetramethylene, or a physiologically acceptable salt thereof.

3. The compound according to claim 1 which is represented by the formula (Ia):

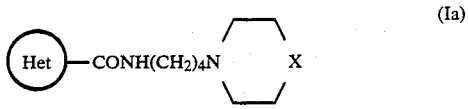

wherein X means the same as defined in claim 1, (Het) means a group of the formula:

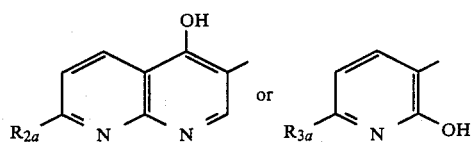

in which $R_{2a}$ and $R_{3a}$ mean an alkyl group having 1 to 4 carbon atoms, or a physiologically acceptable salt thereof.

4. The compound according to claim 1 which is represented by the formula (Ib):

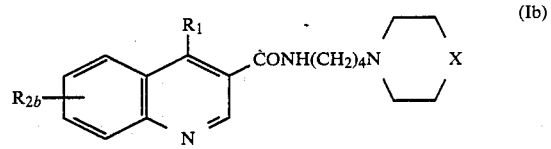

wherein X and $R_1$ mean the same as defined in claim 1, $R_{2b}$ means hydrogen atom, hydroxy, an alkyl group having 1 to 4 carbon atoms, an alkoxy group having 1 to 4 carbon atoms or cyano, or a physiologically acceptable salt thereof.

5. The compound according to claim 3, which is N-[4-(4-diphenylmethylene-1-piperidyl)butyl]-4-hydroxy-7-methyl-1,8-naphthyridine-3-carboxamide or a physiologically acceptable salt thereof.

6. The compound according to claim 3, which is N-[4-(4-diphenylmethyl-1-piperazinyl)butyl]-4-hydroxy-7-methyl-1,8-naphthyridine-3-carboxamide, or a physiologically acceptable salt thereof.

7. The compound according to claim 4, which is N-[4-(4-diphenylmethyl-1-piperazinyl)butyl]-4-hydroxy-8-methoxyquinoline-3-carboxamide, or a physiologically acceptable salt thereof.

8. The compound according to claim 3, which is N-[4-(4-diphenylmethyl-1-piperazinyl)butyl]-2-hydroxy-6-isopropylpyridine-3-carboxamide, or a physiologically acceptable salt thereof.

9. A pharmaceutical composition comprising an antiallergic effective amount of a compound as set forth in claim 1 or a physiologically acceptable salt thereof in admixture with a pharmaceutically acceptable carrier or diluent.

10. A pharmaceutical composition comprising an antiallergic effective amount of a compound as set forth in claim 2 or a physiologically acceptable salt thereof in admixture with a pharmaceutically acceptable carrier or diluent.

11. A pharmaceutical composition comprising an antiallergic effective amount of a compound as set forth in claim 3 or a physiologically acceptable salt thereof in admixture with a pharmaceutically acceptable carrier or diluent.

12. A pharmaceutical composition comprising an antiallergic effective amount of a compound as set forth in claim 4 or a physiologically acceptable salt thereof in admixture with a pharmaceutically acceptable carrier or diluent.

13. A pharmaceutical composition comprising an antiallergic effective amount of a compound as set forth in claim 5 or a physiologically acceptable salt thereof in admixture with a pharmaceutically acceptable carrier or diluent.

14. A pharmaceutical composition comprising an antiallergic effective amount of a compound set forth in claim 6 or a physiologically acceptable salt thereof in admixture with a pharmaceutically acceptable carrier or diluent.

15. A pharmaceutical composition comprising an antiallergic effective amount of a compound as set forth in claim 7 or a physiologically acceptable salt thereof in admixture with a pharmaceutically acceptable carrier or diluent.

16. A pharmaceutical composition comprising an antiallergic effective amount of a compound as set forth in claim 8 or a physiologically acceptable salt thereof in admixture with a pharmaceutically acceptable carrier or diluent.

* * * * *

UNITED STATES PATENT AND TRADEMARK OFFICE
CERTIFICATE OF CORRECTION

PATENT NO. : 4,965,266
DATED : October 23, 1990
INVENTOR(S) : Hitoshi Uno, et al.

It is certified that error appears in the above-identified patent and that said Letters Patent is hereby corrected as shown below:

Column 2, line 54: "Het" should read as --Het'--

Column 11, line 11: "hydratet" should read as --hydrate--

Signed and Sealed this

Fifth Day of May, 1992

Attest:

DOUGLAS B. COMER

Attesting Officer

Acting Commissioner of Patents and Trademarks